(12) United States Patent
Lee et al.

(10) Patent No.: US 8,927,780 B2
(45) Date of Patent: *Jan. 6, 2015

US008927780B2

(54) PROCESS FOR REMOVING ALDEHYDES FROM ETHANOL REACTION MIXTURE

(75) Inventors: David Lee, Seabrook, TX (US); Adam Orosco, Houston, TX (US); Lincoln Sarager, Houston, TX (US); R. Jay Warner, Houston, TX (US); Radmila Jevtic, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 422 days.

This patent is subject to a terminal disclaimer.

(21) Appl. No.: 13/197,749

(22) Filed: Aug. 3, 2011

(65) Prior Publication Data

US 2012/0277487 A1 Nov. 1, 2012

Related U.S. Application Data

(63) Continuation-in-part of application No. 13/094,473, filed on Apr. 26, 2011, now Pat. No. 8,461,399.

(51) Int. Cl.
*C07C 29/149* (2006.01)
*C07C 29/80* (2006.01)

(52) U.S. Cl.
CPC .............. *C07C 29/149* (2013.01); *C07C 29/80* (2013.01)
USPC ......................................... 568/884; 568/885

(58) Field of Classification Search
USPC ................................................ 568/884, 885
See application file for complete search history.

(56) References Cited

U.S. PATENT DOCUMENTS

| | | |
|---|---|---|
| 2,607,719 A | 8/1952 | Eliot et al. |
| 2,649,407 A | 8/1953 | Harrison et al. |
| 2,702,783 A | 2/1955 | Harrison et al. |
| 2,715,604 A | 8/1955 | Weaver et al. |
| 2,801,209 A | 7/1957 | Muller et al. |
| 2,882,244 A | 4/1959 | Milton |
| 3,130,007 A | 4/1964 | Breck |
| 3,408,267 A | 10/1968 | Miller et al. |
| 3,445,345 A | 5/1969 | Katzen et al. |
| 3,478,112 A | 11/1969 | Karl et al. |
| 3,990,952 A | 11/1976 | Katzen et al. |
| 4,275,228 A | 6/1981 | Gruffaz et al. |
| 4,306,942 A | 12/1981 | Brush et al. |
| 4,308,131 A | 12/1981 | Bannon |
| 4,317,918 A | 3/1982 | Takano et al. |
| 4,319,058 A | 3/1982 | Kulprathipanja et al. |
| 4,379,028 A | 4/1983 | Berg et al. |
| 4,395,576 A | 7/1983 | Kwantes et al. |
| 4,398,039 A | 8/1983 | Pesa et al. |
| 4,421,939 A | 12/1983 | Kiff et al. |
| 4,422,903 A | 12/1983 | Messick et al. |
| 4,454,358 A | 6/1984 | Kummer et al. |
| 4,465,854 A | 8/1984 | Pond et al. |
| 4,471,136 A | 9/1984 | Larkins et al. |
| 4,480,115 A | 10/1984 | McGinnis |
| 4,492,808 A | 1/1985 | Hagen et al. |
| 4,497,967 A | 2/1985 | Wan |
| 4,517,391 A | 5/1985 | Schuster et al. |
| 4,520,213 A | 5/1985 | Victor |
| 4,541,897 A | 9/1985 | Sommer et al. |
| 4,569,726 A | 2/1986 | Berg et al. |
| 4,626,321 A | 12/1986 | Grethlein et al. |
| 4,678,543 A | 7/1987 | Houben et al. |
| 4,692,218 A | 9/1987 | Houben et al. |
| 4,777,303 A | 10/1988 | Kitson et al. |
| 4,804,791 A | 2/1989 | Kitson et al. |
| 4,842,693 A | 6/1989 | Wheldon |
| 4,961,826 A | 10/1990 | Grethlein et al. |
| 4,985,572 A | 1/1991 | Kitson et al. |
| 4,990,655 A | 2/1991 | Kitson et al. |
| 4,994,608 A | 2/1991 | Torrence et al. |
| 5,001,259 A | 3/1991 | Smith et al. |
| 5,026,908 A | 6/1991 | Smith et al. |
| 5,035,776 A | 7/1991 | Knapp et al. |
| 5,061,671 A | 10/1991 | Kitson et al. |
| 5,124,004 A | 6/1992 | Grethlein et al. |
| 5,144,068 A | 9/1992 | Smith et al. |
| 5,149,680 A | 9/1992 | Kitson et al. |
| 5,185,481 A | 2/1993 | Muto et al. |
| 5,215,902 A | 6/1993 | Tedder |
| 5,227,141 A | 7/1993 | Kim et al. |
| 5,233,099 A | 8/1993 | Tabata et al. |
| 5,237,108 A | 8/1993 | Marraccini et al. |
| 5,250,271 A | 10/1993 | Horizoe et al. |

(Continued)

FOREIGN PATENT DOCUMENTS

| | | |
|---|---|---|
| EP | 0056488 | 7/1982 |
| EP | 0104197 | 4/1984 |

(Continued)

OTHER PUBLICATIONS

Zheng, et al. (2007). Preparation and catalytic properties of a bimetallic Sn—Pt complex in the supercages of NaY zeolite by use of surface organometallic chemistry, Applied Organometallic Chemistry, 21(10), 836-840.
ZeaChem, Inc., Technology Overview, Lakewood, Colorado www.zeachem.com, 2008.
Santori et al.(2000). Hydrogenation of carbonylic compounds on Pt/SiO2 catalysts modified with SnBu4, Studies in Surface Science and Catalysis, 130, 2063-2068.
Rachmady, Acetic Acid Reduction by H2 on Bimetallic Pt—Fe Catalysts, Journal of Catalysis 209, 87-98 (Apr. 1, 2002), Elsevier Science (USA).
Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.
Hilmen, Separation of Azeotropic Mixtures: Tools for Analysis and Studies on Batch Distillation Operation (Nov. 2000) p. 17-20.

(Continued)

*Primary Examiner* — Elvis O Price

(57) ABSTRACT

A process for purifying an ethanol stream that comprises byproduct, such as aldehyde, acetals, and/or esters, but withdrawing a sidestream comprising ethanol from a distillation column. The sidestream may have a reduced concentration of aldehyde that reduces the formation of acetals in subsequent purification of the ethanol stream.

16 Claims, 3 Drawing Sheets

(56) References Cited

U.S. PATENT DOCUMENTS

| | | |
|---|---|---|
| 5,348,625 A | 9/1994 | Berg |
| 5,415,741 A | 5/1995 | Berg |
| 5,437,770 A | 8/1995 | Berg |
| 5,445,716 A | 8/1995 | Berg |
| 5,449,440 A | 9/1995 | Rescalli et al. |
| RE35,377 E | 11/1996 | Steinberg et al. |
| 5,599,976 A | 2/1997 | Scates et al. |
| 5,762,765 A | 6/1998 | Berg |
| 5,770,770 A | 6/1998 | Kim et al. |
| 5,800,681 A | 9/1998 | Berg |
| 5,821,111 A | 10/1998 | Gaddy et al. |
| 5,993,610 A | 11/1999 | Berg |
| 6,121,498 A | 9/2000 | Tustin et al. |
| 6,143,930 A | 11/2000 | Singh et al. |
| 6,232,352 B1 | 5/2001 | Vidalin et al. |
| 6,294,703 B1 | 9/2001 | Hara et al. |
| 6,375,807 B1 | 4/2002 | Nieuwoudt et al. |
| 6,509,180 B1 | 1/2003 | Verser et al. |
| 6,627,770 B1 | 9/2003 | Cheung et al. |
| 6,657,078 B2 | 12/2003 | Scates et al. |
| 6,685,754 B2 | 2/2004 | Kindig et al. |
| 6,693,213 B1 | 2/2004 | Kolena et al. |
| 6,723,886 B2 | 4/2004 | Allison et al. |
| 6,906,228 B2 | 6/2005 | Fischer et al. |
| 6,927,048 B2 | 8/2005 | Verser et al. |
| 7,005,541 B2 | 2/2006 | Cheung et al. |
| 7,074,603 B2 | 7/2006 | Verser et al. |
| 7,115,772 B2 | 10/2006 | Picard et al. |
| 7,208,624 B2 | 4/2007 | Scates et al. |
| 7,297,236 B1 | 11/2007 | Vander et al. |
| 7,351,559 B2 | 4/2008 | Verser et al. |
| 7,399,892 B2 | 7/2008 | Rix et al. |
| 7,507,562 B2 | 3/2009 | Verser et al. |
| 7,553,397 B1 | 6/2009 | Colley et al. |
| 7,572,353 B1 | 8/2009 | Vander et al. |
| 7,601,865 B2 | 10/2009 | Verser et al. |
| 7,608,744 B1 | 10/2009 | Johnston et al. |
| 7,682,812 B2 | 3/2010 | Verser et al. |
| 7,700,814 B2 | 4/2010 | Garton et al. |
| 7,732,173 B2 | 6/2010 | Mairal et al. |
| 7,744,727 B2 | 6/2010 | Blum et al. |
| 7,863,489 B2 | 1/2011 | Johnston et al. |
| 7,884,253 B2 | 2/2011 | Stites et al. |
| 7,888,082 B2 | 2/2011 | Verser et al. |
| 2006/0019360 A1 | 1/2006 | Verser et al. |
| 2006/0127999 A1 | 6/2006 | Verser et al. |
| 2007/0270511 A1 | 11/2007 | Melnichuk et al. |
| 2008/0135396 A1 | 6/2008 | Blum |
| 2008/0193989 A1 | 8/2008 | Verser et al. |
| 2009/0014313 A1 | 1/2009 | Lee et al. |
| 2009/0023192 A1 | 1/2009 | Verser et al. |
| 2009/0069609 A1 | 3/2009 | Kharas et al. |
| 2009/0081749 A1 | 3/2009 | Verser et al. |
| 2009/0166172 A1 | 7/2009 | Casey et al. |
| 2009/0281354 A1 | 11/2009 | Mariansky et al. |
| 2009/0318573 A1 | 12/2009 | Stites et al. |
| 2010/0029980 A1 | 2/2010 | Johnston et al. |
| 2010/0029995 A1 | 2/2010 | Johnston et al. |
| 2010/0030001 A1 | 2/2010 | Chen et al. |
| 2010/0030002 A1 | 2/2010 | Johnston et al. |
| 2010/0121114 A1 | 5/2010 | Johnston et al. |
| 2010/0197485 A1 | 8/2010 | Johnston et al. |
| 2011/0028767 A1 | 2/2011 | Kikuchi et al. |
| 2011/0082322 A1 | 4/2011 | Jevtic et al. |

FOREIGN PATENT DOCUMENTS

| | | |
|---|---|---|
| EP | 0120269 | 10/1984 |
| EP | 0167300 | 1/1986 |
| EP | 0234508 | 9/1987 |
| EP | 0456647 | 11/1991 |
| EP | 0992484 | 4/2000 |
| EP | 2060553 | 5/2009 |
| EP | 2060555 | 5/2009 |
| EP | 2072487 | 6/2009 |
| EP | 2072488 | 6/2009 |
| EP | 2072489 | 6/2009 |
| EP | 2072492 | 6/2009 |
| EP | 2186787 | 5/2010 |
| GB | 2053915 | 2/1981 |
| JP | 4193304 | 7/1992 |
| WO | WO 83/03409 | 10/1983 |
| WO | WO 2008/135192 | 11/2008 |
| WO | WO 2009/009322 | 1/2009 |
| WO | WO 2009/009323 | 1/2009 |
| WO | WO 2009/048335 | 4/2009 |
| WO | WO 2009/063176 | 5/2009 |
| WO | WO 2010/055285 | 5/2010 |

OTHER PUBLICATIONS

Gursahani et al., Reaction kinetics measurements and analysis of reaction pathways for conversions of acetic acid, ethanol, and ethyl acetate over silica-supported Pt, Applied Catalysis A: General 222 (2001) 369-392.

Amit M. Goda et al., DFT modeling of selective reduction of acetic acid to acetaldehyde on Pt-based bimetallic catalysts, 20th NAM, Houston, TX, Jun. 17-22, 2007 available online at <http://www.nacatsoc.org/20nam/abstracts/O-S9-18.pdf>.

Acala, et al., (2005). Experimental and DFT studies of the conversion of ethanol and acetic acid on PtSn-based catalysts, Journal of Physical Chemistry, 109(6), 2074-2085.

International Preliminary Report on Patentability for PCT/US2011/046490 mailed Nov. 7, 2013.

Invitation to Pay Additional Fees and Partial Search Report for PCT/US2011/046490 mailed Aug. 2, 2012.

International Search Report and Written Opinion for PCT/US2011/046490 mailed Oct. 8, 2012.

International Search Report and Written Opinion for PCT/US2011/059901 mailed Aug. 2, 2012.

Office Action for corresponding U.S. Appl. No. 13/094,473 dated Dec. 6, 2012.

PROCESS FOR REMOVING ALDEHYDES FROM ETHANOL REACTION MIXTURE

CROSS REFERENCE TO RELATED APPLICATION

The present application is a continuation-in-part application of U.S. patent Ser. No. 13/094,473, filed on Apr. 26, 2011, the entire contents and disclosure of which is hereby incorporated by reference.

FIELD OF THE INVENTION

The present invention relates generally to processes for producing ethanol and, in particular, to purifying an ethanol product by removing impurities, such as aldehydes, from the ethanol reaction mixture.

BACKGROUND OF THE INVENTION

Ethanol for industrial use is conventionally produced from petrochemical feed stocks, such as oil, natural gas, or coal, from feed stock intermediates, such as syngas, or from starchy materials or cellulose materials, such as corn or sugar cane. Conventional methods for producing ethanol from petrochemical feed stocks, as well as from cellulose materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulose material, are converted to ethanol by fermentation. However, fermentation is typically used for consumer production of ethanol, which is suitable for fuels or human consumption. In addition, fermentation of starchy or cellulose materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. During the reduction of alkanoic acid, e.g., acetic acid, other compounds are formed with ethanol or are formed in side reactions. These impurities limit the production and recovery of ethanol from such reaction mixtures. For example, during hydrogenation, esters are produced that together with ethanol and/or water form azeotropes, which are difficult to separate. In addition when conversion is incomplete, unreacted acid remains in the crude ethanol product, which must be removed to recover ethanol.

EP02060553 describes a process for converting hydrocarbons to ethanol involving converting the hydrocarbons to ethanoic acid and hydrogenating the ethanoic acid to ethanol. The stream from the hydrogenation reactor is separated to obtain an ethanol product and a stream of acetic acid and ethyl acetate, which is recycled to the hydrogenation reactor.

The need remains for improved processes for recovering ethanol from a crude product obtained by reducing alkanoic acids, such as acetic acid, and/or other carbonyl group-containing compounds.

SUMMARY OF THE INVENTION

In a first embodiment, the present invention is directed to a process for producing ethanol comprising hydrogenating a feed stream comprising an alkanoic acid and/or an ester thereof in the presence of a catalyst in a reactor to form a crude ethanol product comprising ethanol, ethyl acetate, water, and acetaldehyde; separating at least a portion of the crude ethanol product in a first distillation column into a first distillate comprising acetaldehyde, a sidestream comprising ethanol, and ethyl acetate, and a first residue stream comprising water; and recovering ethanol from the sidestream.

In a second embodiment, the present invention is directed to a process for producing ethanol comprising hydrogenating a feed stream comprising an alkanoic acid and/or an ester thereof in the presence of a catalyst in a reactor to form a crude ethanol product comprising ethanol, ethyl acetate, alkanoic acid, and acetaldehyde; separating at least a portion of the crude ethanol product in a first distillation column into a first distillate comprising acetaldehyde, a sidestream comprising ethanol, and ethyl acetate, and a first residue stream comprising alkanoic acid; and recovering ethanol from the sidestream.

In a third embodiment, the present invention is directed to a process for producing ethanol comprising hydrogenating a feed stream comprising an alkanoic acid and/or an ester thereof in the presence of a catalyst in a reactor to form a crude ethanol product comprising ethanol, ethyl acetate, water, acetaldehyde, and diethyl acetal; obtaining a sidestream comprising ethanol, and ethyl acetate from at least a portion of the crude ethanol product from a first distillation column, wherein at least 10 to 75% of the diethyl acetal fed to the first distillation column is decomposed in the first distillation column; and recovering ethanol from the sidestream.

In a fourth embodiment, the present invention is directed to a process for producing ethanol comprising providing a crude ethanol product comprising ethanol, ethyl acetate, alkanoic acid, water, and acetaldehyde; separating at least a portion of the crude ethanol product in a first distillation column into a first distillate comprising acetaldehyde, a sidestream comprising ethanol, and ethyl acetate, and a first residue stream comprising alkanoic acid and water; and recovering ethanol from the sidestream.

In a fifth embodiment, the present invention is directed to a process for producing ethanol comprising hydrogenating an feed stream comprising an alkanoic acid and/or an ester thereof in the presence of a catalyst in a reactor to form a crude ethanol product comprising ethanol, ethyl acetate, water, and acetaldehyde; separating at least a portion of the crude ethanol product in a first distillation column into an overhead stream comprising ethanol, ethyl acetate, and acetaldehyde, and a first residue stream comprising water; and partially condensing a portion of the first distillate stream and separating the partially condensed first distillate stream into a non-condensed stream comprising acetaldehyde and a condensed distillate comprising ethanol and ethyl acetate; and recovering ethanol from the condensed distillate.

BRIEF DESCRIPTION OF DRAWINGS

The invention is described in detail below with reference to the appended drawings, wherein like numerals designate similar parts.

DETAILED DESCRIPTION OF THE INVENTION

Introduction

Figure 1:
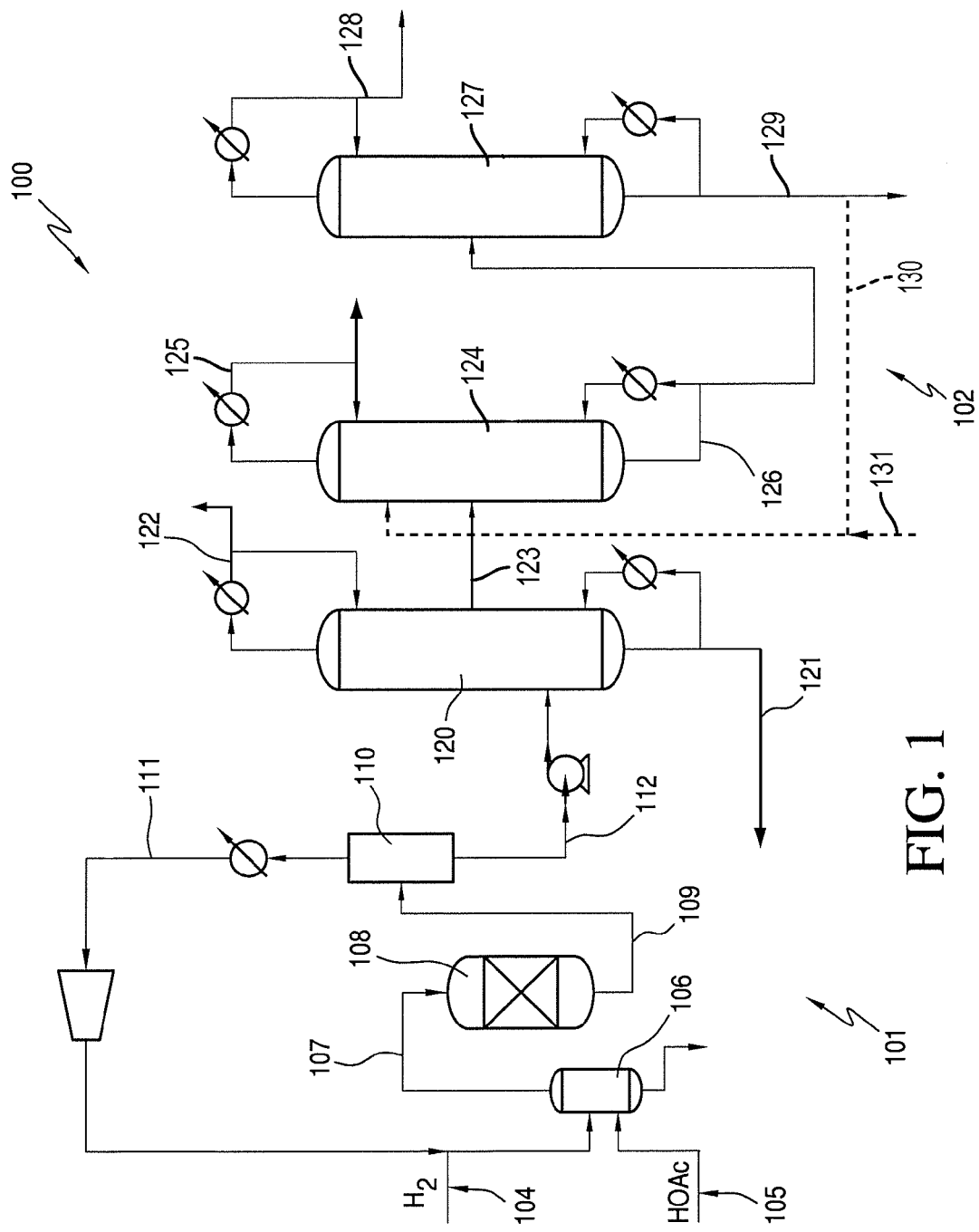
FIG. 1 is a schematic diagram of a process to purify a crude ethanol product using a sidestream, in accordance with an embodiment of the present invention.

The present invention relates to processes for producing alcohols produced by hydrogenating alkanoic acid, such as acetic acid, and/or esters thereof in the presence of a catalyst. The reaction mixture produced by the hydrogenation reaction comprises the desired alcohols, such as ethanol, as well as several byproducts including but not limited to esters, aldehydes, and acetals. In some embodiments, the alkanoic acid may also need to be removed along with any water. When acetic acid is hydrogenated, the reaction mixture may comprise ethanol, acetic acid, water, ethyl acetate, acetaldehyde, and/or diethyl acetal.

Depending on the ethanol application, certain byproducts in the reaction mixture may need to be removed below acceptable limits when purifying ethanol. However, during the purification of the reaction mixture, as some byproducts are removed other byproducts may be formed. Thus, removal of certain byproducts may be difficult during purification. Depending on the system, additional energy may be required to achieve the sufficiently low levels of byproducts, which leads to inefficiencies. In particular, diethyl acetal (DEA) may be formed by reacting acetaldehyde and ethanol during the purification. When DEA is formed in the purification there may be a decrease in efficiency in recovering ethanol as well as decreases in ethanol yields. The present invention provides a process for removing the byproducts as well as reducing the formation of the byproducts in the purification of the reaction mixture. In one embodiment, a portion of the acetaldehyde in the reaction mixture is removed to reduce the formation of diethyl acetal in subsequent columns when recovering ethanol. Advantageously, the reduction of acetaldehyde concentration may favor hydrolysis of acetals, such as diethyl acetal, in subsequent distillation columns. This would also lead to a reduction of diethyl acetal concentration in the purification system, as well as beneficially reducing the diethyl acetal concentration in the ethanol product.

In one embodiment, the reaction mixture or a liquid portion of the reaction mixture is fed to an initial column in the purification system. The column separates the reaction mixture into an overhead stream that comprises a portion of the acetaldehyde, a sidestream, e.g., ethanol intermediate stream, that comprises a majority of the ethanol, and a residue that comprises acetic acid. In one aspect the residue may comprise a substantial portion of the water fed to the initial column in addition to the acetic acid. The sidestream may be further processed in one or more distillation columns, membranes, adsorption units to remove any byproducts, such as ethyl acetate, water, diethyl acetal, acetaldehyde, or acetic acid. In some embodiments, the overhead stream may also comprise ethyl acetate, ethanol, and/or water.

In another embodiment, the reaction mixture or a liquid portion of the reaction mixture is fed to an initial column in the purification system. The column separates the reaction mixture into an overhead stream that comprises acetaldehyde and ethanol. The overhead stream is partially condensed and a vent stream is withdrawn from the partial condenser. The vent stream may comprise a portion of the acetaldehyde and the remaining condensed overhead comprises ethanol and a reduced amount of acetaldehyde. The condensed overhead, e.g., ethanol intermediate stream, may be further processed in one or more distillation columns, membranes, adsorption units to remove any further byproducts, such as ethyl acetate, water, diethyl acetal, acetaldehyde, or acetic acid. In some embodiments, the vent stream may also comprise ethyl acetate, ethanol, and/or water.

The initial column is operated such that the ethanol intermediate stream comprises less than 2 wt. % acetic acid, e.g., less than 0.1 wt. % or more preferably less than 0.05 wt. %. This reduces the need to further separate the acetic acid from the ethanol and may also prevent subsequent esterification reactions. In addition, the initial column is operated such there are small ethanol concentrations in the residue of the initial column, preferably less than 1 wt. %, less than 0.5 wt. % or less than 0.1 wt. %. Depending on the treatment of the residue, the residue may not be recycled to the reactor and the ethanol in the residue may decrease the overall yield of ethanol. Low ethanol concentrations in residue allow for higher ethanol recovery rates, of at least 80% of the ethanol in the reaction mixture, e.g., at least 90% of the ethanol or at least 95% of the ethanol.

Preferably, the ethanol intermediate stream comprises reduced acetaldehyde concentrations as compared to processes that have no ethanol sidestream or no partial condenser. The acetaldehyde concentration in the ethanol intermediate stream may vary and may be less than 5 wt. %, e.g., less than 2 wt. % or less than 0.5 wt. %.

Without being bound by theory, the initial column of the present invention is operated such that when any amount of acetal, such as diethyl acetal, is present in the feed introduced to the distillation column, the acetal may decompose in the column. The diethyl acetal may be, for example, hydrolyzed to form acetaldehyde and ethanol. In one embodiment, from 10 to 75% of the diethyl acetal is decomposed in the initial column, e.g., from 15 to 60% or more preferably from 20 to 40%. Hence, smaller detectable amounts of the acetal are present in the streams exiting the column, including overhead stream, sidestream and/or residue stream. The total detectable acetal concentration in the streams is less than the acetal concentration fed to the column. Thus, the present invention may reduce the amount of diethyl acetal in ethanol intermediate stream that needs to be further separated after the initial column.

The ethanol intermediate stream from the initial column, e.g. sidestream or partially condensed overhead, is preferably fed to a second distillation column. The second distillation column may remove light organics from the ethanol intermediate stream such as ethyl acetate, acetaldehyde, and/or diethyl acetal. Preferably ethanol is recovered from the second distillation column and the total concentration of byproducts, such as ethyl acetate, acetaldehyde, and/or diethyl acetal, that is recovered with the ethanol is preferably less than 1 wt. %, e.g., less than 0.5 wt. % or less than 0.01 wt. %. Reducing the amount of acetaldehyde fed to the second column may advantageously reduce the diethyl acetal concentration in the recovered ethanol. In addition, the hydrolysis of diethyl acetal may be favored in the second column.

In some embodiments, a water separator may be used between the distillations columns to remove water from the ethanol intermediate stream. The water separator may include extractive distillation columns, adsorption units, membranes, or molecular sieves. Suitable adsorption units include pressure swing adsorption units and thermal swing adsorption units.

Hydrogenation Reaction

The process of the present invention may be used with any hydrogenation process for producing ethanol. The materials, catalysts, reaction conditions, and separation processes that may be used in the hydrogenation of acetic acid are described further below.

The raw materials, such as alkanoic acids and hydrogen, fed to the hydrogenation reactor used in connection with the process of this invention may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference. Optionally, the production of ethanol may be integrated with such methanol carbonylation processes.

As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive, it may become advantageous to produce acetic acid from synthesis gas ("syngas") that is derived from more available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum*, and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. Nos. 6,509,180; 6,927,048; 7,074,603; 7,507,562; 7,351,559; 7,601,865; 7,682,812; and 7,888,082, the entireties of which are incorporated herein by reference. See also U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884,253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a synthesis gas including hydrogen and carbon monoxide, are incorporated herein by reference in their entireties.

The acetic acid fed to the hydrogenation reactor may also comprise other carboxylic acids and anhydrides, as well as acetaldehyde and acetone. Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the presence of carboxylic acids, such as propanoic acid or its anhydride, may be beneficial in producing propanol. Water may also be present in the acetic acid feed.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the hydrogenation reactor without the need for condensing the acetic acid and light ends or removing water, saving overall processing costs.

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

The reactor, in some embodiments, may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed as the reactor, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation in the reactor may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 kPa to 3000 kPa, e.g., from 50 kPa to 2300 kPa, or from 100 kPa to 1500 kPa. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^{-1}$ or 6,500 $hr^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 12:1 to 1:1. Most preferably, the molar ratio of hydrogen to acetic acid is greater than 2:1, e.g., greater than 4:1 or greater than 8:1. Generally, the reactor may use an excess of hydrogen.

Contact or residence time can also vary widely, depending upon such variables as amount of acetic acid, catalyst, reactor, temperature, and pressure. Typical contact times range from a fraction of a second to more than several hours when a catalyst system other than a fixed bed is used, with preferred contact times, at least for vapor phase reactions, of from 0.1 to 100 seconds, e.g., from 0.3 to 80 seconds or from 0.4 to 30 seconds.

The hydrogenation of acetic acid to form ethanol is preferably conducted in the presence of a hydrogenation catalyst in the hydrogenation reactor. Suitable hydrogenation catalysts include catalysts comprising a first metal and optionally one or more of a second metal, a third metal or any number of additional metals, optionally on a catalyst support. The first and optional second and third metals may be selected from Group IB, IIB, IIIB, IVB, VB, VIB, VIIB, VIII transition metals, a lanthanide metal, an actinide metal or a metal selected from any of Groups IIIA, IVA, VA, and VIA. Preferred metal combinations for some exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, cobalt/tin, silver/palladium, copper/palladium, copper/zinc, nickel/palladium, gold/palladium, ruthenium/rhenium, and ruthenium/iron. Exemplary catalysts are further described in U.S. Pat. No. 7,608,744 and U.S. Pub. No. 2010/0029995, the entireties of which are incorporated herein by reference. In another embodiment, the catalyst comprises a Co/Mo/S catalyst of the type described in U.S. Pub. No. 2009/0069609, the entirety of which is incorporated herein by reference.

In one embodiment, the catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium. More preferably, the first metal is selected from platinum and palladium. In embodiments of the invention where the first metal comprises platinum, it is preferred that the catalyst comprises platinum in an amount less than 5 wt. %, e.g., less than 3 wt. % or less than 1 wt. %, due to the high commercial demand for platinum.

As indicated above, in some embodiments, the catalyst further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel. More preferably, the second metal is selected from tin and rhenium.

In certain embodiments where the catalyst includes two or more metals, e.g., a first metal and a second metal, the first metal is present in the catalyst in an amount from 0.1 to 10 wt. %, e.g., from 0.1 to 5 wt. %, or from 0.1 to 3 wt. %. The second metal preferably is present in an amount from 0.1 to 20 wt. %, e.g., from 0.1 to 10 wt. %, or from 0.1 to 5 wt. %. For catalysts comprising two or more metals, the two or more metals may be alloyed with one another or may comprise a non-alloyed metal solution or mixture.

The preferred metal ratios may vary depending on the metals used in the catalyst. In some exemplary embodiments, the mole ratio of the first metal to the second metal is from 10:1 to 1:10, e.g., from 4:1 to 1:4, from 2:1 to 1:2, from 1.5:1 to 1:1.5 or from 1.1:1 to 1:1.1.

The catalyst may also comprise a third metal selected from any of the metals listed above in connection with the first or second metal, so long as the third metal is different from the first and second metals. In preferred aspects, the third metal is selected from the group consisting of cobalt, palladium, ruthenium, copper, zinc, platinum, tin, and rhenium. More preferably, the third metal is selected from cobalt, palladium, and ruthenium. When present, the total weight of the third metal preferably is from 0.05 to 4 wt. %, e.g., from 0.1 to 3 wt. %, or from 0.1 to 2 wt. %.

In addition to one or more metals, in some embodiments of the present invention the catalysts further comprise a support or a modified support. As used herein, the term "modified support" refers to a support that includes a support material and a support modifier, which adjusts the acidity of the support material.

The total weight of the support or modified support, based on the total weight of the catalyst, preferably is from 75 to 99.9 wt. %, e.g., from 78 to 97 wt. %, or from 80 to 95 wt. %. In preferred embodiments that utilize a modified support, the support modifier is present in an amount from 0.1 to 50 wt. %, e.g., from 0.2 to 25 wt. %, from 0.5 to 15 wt. %, or from 1 to 8 wt. %, based on the total weight of the catalyst. The metals of the catalysts may be dispersed throughout the support, layered throughout the support, coated on the outer surface of the support (i.e., egg shell), or decorated on the surface of the support.

As will be appreciated by those of ordinary skill in the art, support materials are selected such that the catalyst system is suitably active, selective and robust under the process conditions employed for the formation of ethanol.

Suitable support materials may include, for example, stable metal oxide-based supports or ceramic-based supports. Preferred supports include silicaceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

As indicated, the catalyst support may be modified with a support modifier. In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, and $Sb_2O_3$. Preferred acidic support modifiers include those selected from the group consisting of $TiO_2$, $ZrO_2$, $Nb_2O_5$, $Ta_2O_5$, and $Al_2O_3$. The acidic modifier may also include $WO_3$, $MoO_3$, $Fe_2O_3$, $Cr_2O_3$, $V_2O_5$, $MnO_2$, $CuO$, $Co_2O_3$, and $Bi_2O_3$.

In another embodiment, the support modifier may be a basic modifier that has a low volatility or no volatility. Such basic modifiers, for example, may be selected from the group consisting of: (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. Preferably, the support modifier is selected from the group consisting of oxides and metasilicates of any of sodium, potassium, magnesium, calcium, scandium, yttrium, and zinc, as well as mixtures of any of the foregoing. More preferably, the basic support modifier is a calcium silicate, and even more preferably calcium metasilicate ($CaSiO_3$). If the basic support modifier comprises calcium metasilicate, it is preferred that at least a portion of the calcium metasilicate is in crystalline form.

A preferred silica support material is SS61138 High Surface Area (HSA) Silica Catalyst Carrier from Saint-Gobain NorPro. The Saint-Gobain NorPro SS61138 silica exhibits the following properties: contains approximately 95 wt. % high surface area silica; surface area of about 250 $m^2/g$; median pore diameter of about 12 nm; average pore volume of about 1.0 $cm^3/g$ as measured by mercury intrusion porosimetry and a packing density of about 0.352 $g/cm^3$ (22 $lb/ft^3$).

A preferred silica/alumina support material is KA-160 silica spheres from Sud Chemie having a nominal diameter of about 5 mm, a density of about 0.562 g/ml, an absorptivity of about 0.583 g $H_2O$/g support, a surface area of about 160 to 175 $m^2/g$, and a pore volume of about 0.68 ml/g.

The catalyst compositions suitable for use with the present invention preferably are formed through metal impregnation of the modified support, although other processes such as chemical vapor deposition may also be employed. Such impregnation techniques are described in U.S. Pat. Nos. 7,608,744 and 7,863,489 and U.S. Pub. No. 2010/0197485 referred to above, the entireties of which are incorporated herein by reference.

In particular, the hydrogenation of acetic acid may achieve favorable conversion of acetic acid and favorable selectivity and productivity to ethanol in the reactor. For purposes of the present invention, the term "conversion" refers to the amount of acetic acid in the feed that is converted to a compound other than acetic acid. Conversion is expressed as a mole percentage based on acetic acid in the feed. The conversion may be at least 10%, e.g., at least 20%, at least 40%, at least 50%, at least 60%, at least 70% or at least 80%. Although catalysts that have high conversions are desirable, such as at least 80% or at least 90%, in some embodiments a low conversion may be acceptable at high selectivity for ethanol. It is, of course, well understood that in many cases, it is possible to compensate for conversion by appropriate recycle streams or use of larger reactors, but it is more difficult to compensate for poor selectivity.

Selectivity is expressed as a mole percent based on converted acetic acid. It should be understood that each compound converted from acetic acid has an independent selectivity and that selectivity is independent from conversion. For example, if 60 mole % of the converted acetic acid is converted to ethanol, we refer to the ethanol selectivity as 60%. Preferably, the catalyst selectivity to ethoxylates is at least 60%, e.g., at least 70%, or at least 80%. As used herein, the term "ethoxylates" refers specifically to the compounds ethanol, acetaldehyde, and ethyl acetate. Preferably, in the reactor, the selectivity to ethanol is at least 80%, e.g., at least 85% or at least 88%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 100 grams of ethanol per kilogram of catalyst per hour, e.g., at least 400 grams of ethanol per kilogram of catalyst per hour or at least 600 grams of ethanol per kilogram of catalyst per hour, is preferred. In terms of ranges, the productivity preferably is from 100 to 3,000 grams of ethanol per kilogram of catalyst per hour, e.g., from 400 to 2,500 grams of ethanol per kilogram of catalyst per hour or from 600 to 2,000 grams of ethanol per kilogram of catalyst per hour.

Operating under the conditions of the present invention may result in ethanol production on the order of at least 0.1 tons of ethanol per hour, e.g., at least 1 ton of ethanol per hour, at least 5 tons of ethanol per hour, or at least 10 tons of ethanol per hour. Larger scale industrial production of ethanol, depending on the scale, generally should be at least 1 ton of ethanol per hour, e.g., at least 15 tons of ethanol per hour or at least 30 tons of ethanol per hour. In terms of ranges, for large scale industrial production of ethanol, the process of the present invention may produce from 0.1 to 160 tons of ethanol per hour, e.g., from 15 to 160 tons of ethanol per hour or from 30 to 80 tons of ethanol per hour. Ethanol production from fermentation, due the economies of scale, typically does not permit the single facility ethanol production that may be achievable by employing embodiments of the present invention.

In various embodiments of the present invention, the crude ethanol product produced by the reactor, before any subsequent processing, such as purification and separation, will typically comprise unreacted acetic acid, ethanol and water. As used herein, the term "crude ethanol product" refers to any composition comprising from 5 to 70 wt. % ethanol and from 5 to 40 wt. % water. Exemplary compositional ranges for the crude ethanol product are provided in Table 1. The "others" identified in Table 1 may include, for example, esters, ethers, aldehydes, ketones, alkanes, and carbon dioxide.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 70 | 15 to 70 | 15 to 50 | 25 to 50 |
| Acetic Acid | 0 to 90 | 0 to 50 | 15 to 70 | 20 to 70 |
| Water | 5 to 40 | 5 to 30 | 10 to 30 | 10 to 26 |
| Ethyl Acetate | 0 to 30 | 0 to 20 | 1 to 12 | 3 to 10 |
| Acetaldehyde | 0 to 10 | 0 to 3 | 0.1 to 3 | 0.2 to 2 |
| Others | 0.1 to 10 | 0.1 to 6 | 0.1 to 4 | — |

In one embodiment, the crude ethanol product may comprise acetic acid in an amount less than 20 wt. %, e.g., of less than 15 wt. %, less than 10 wt. % or less than 5 wt. %. In embodiments having lower amounts of acetic acid, the conversion of acetic acid is preferably greater than 75%, e.g., greater than 85% or greater than 90%. In addition, the selectivity to ethanol may also be preferably high, and is greater than 75%, e.g., greater than 85% or greater than 90%.

Ethanol Separation

Figure 2:
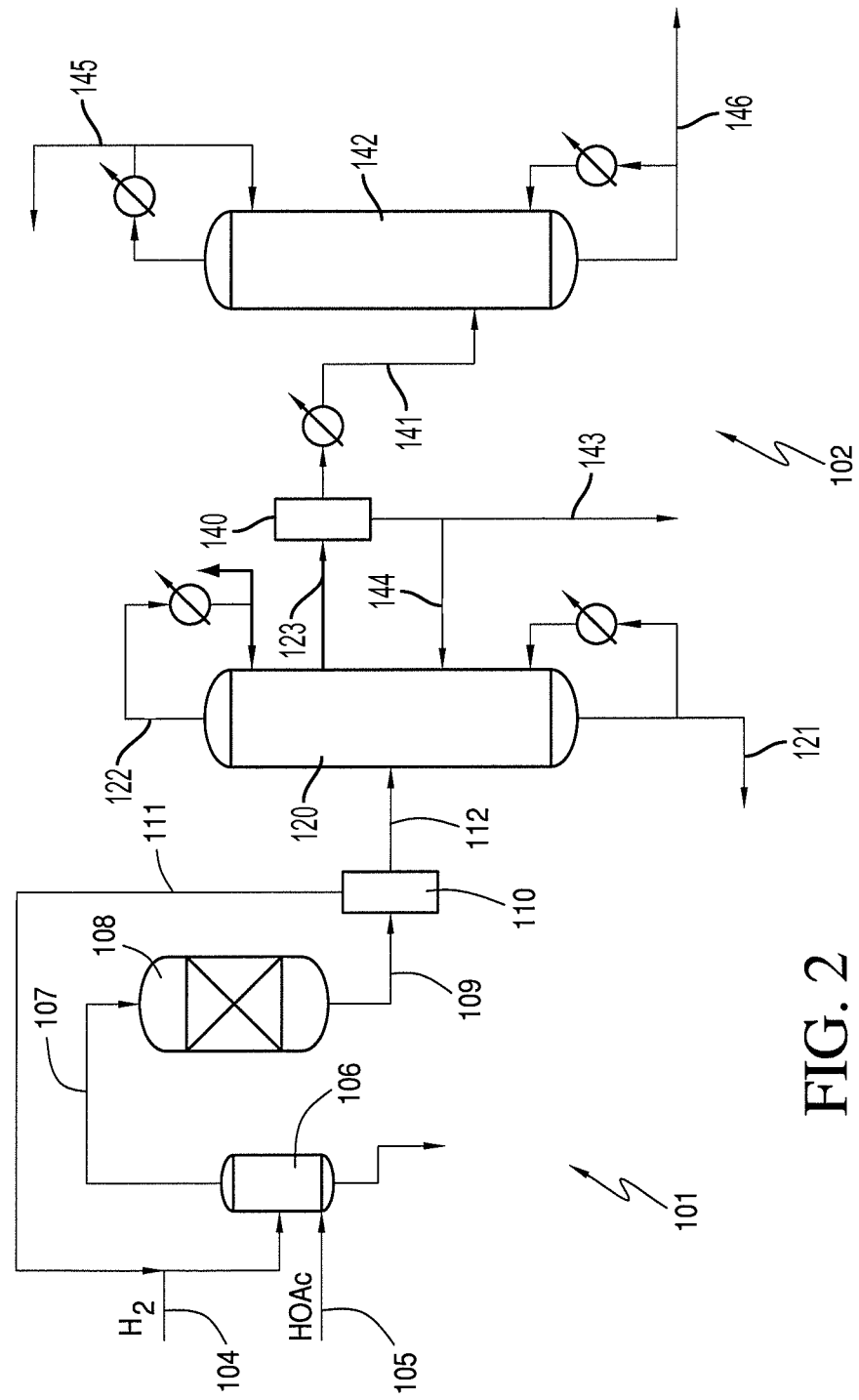
FIG. 2 is a schematic diagram of a process to purify a crude ethanol product using a sidestream and an intervening water removal, in accordance with an alternative embodiment of the present invention.
Figure 3:
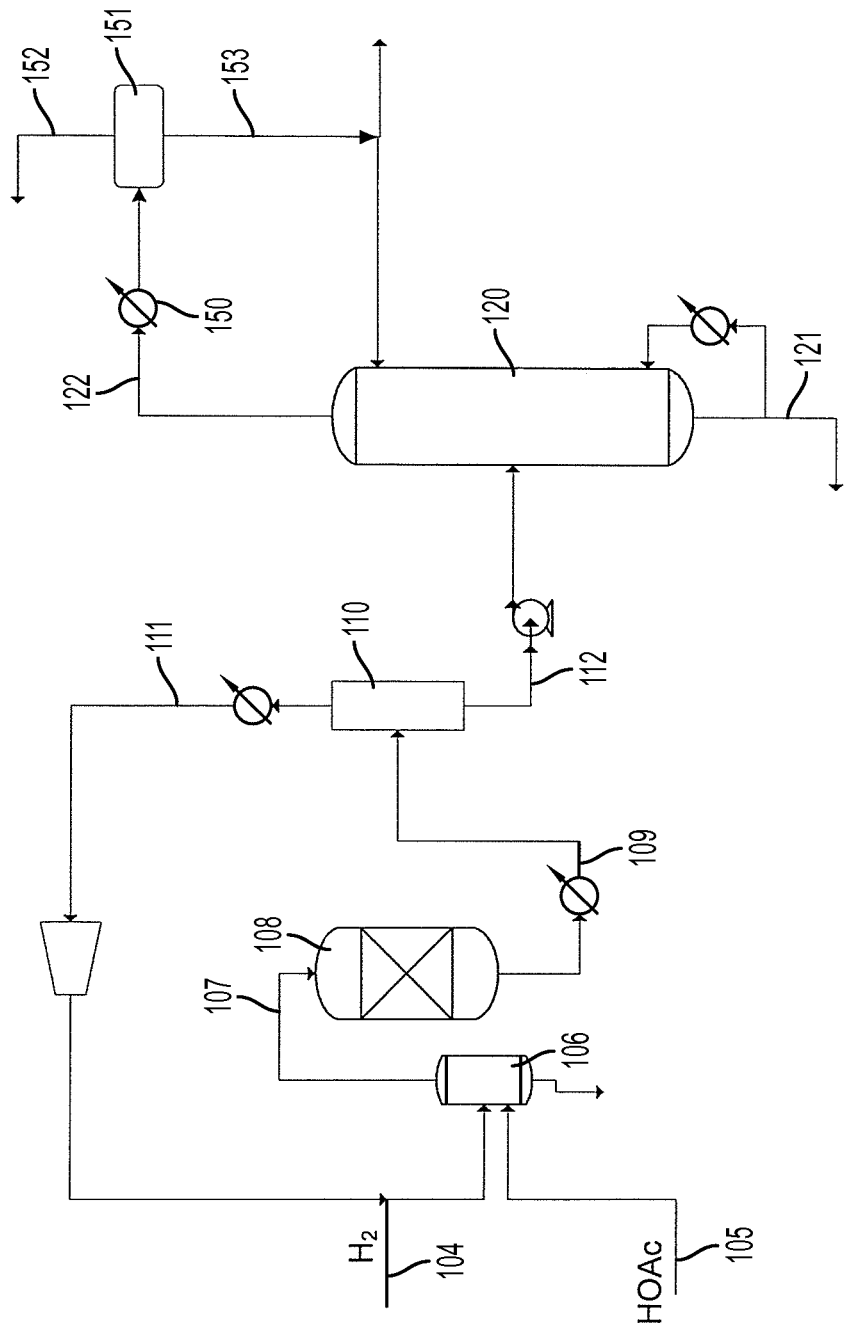
FIG. 3 is a schematic diagram of a process to purify a crude ethanol product by partially condensing the overhead of the first stream and removing a vent stream comprising acetaldehyde, in accordance with an alternative embodiment of the present invention.

Ethanol produced by the reactor may be recovered using several different techniques. Several exemplary techniques that produce an intermediate stream are shown in the figures. The intermediate stream, sidestream or condensed overhead, is fed to one or more secondary reactors to reduce the concentration of impurities and produce an ethanol product. In FIG. 1, the separation of the crude ethanol product uses three columns. In FIG. 2, the crude ethanol product is separated in two columns with an intervening water separation. In FIG. 3, acetaldehyde may be removed from a partial condenser. Other separation systems may also be used with embodiments of the present invention.

Hydrogenation system 100 includes a reaction zone 101, and a separation zone 102. Hydrogen and acetic acid via lines 104 and 105, respectively, are fed to a vaporizer 106 to create a vapor feed stream in line 107 that is directed to reactor 108. In one embodiment, lines 104 and 105 may be combined and jointly fed to the vaporizer 106. The temperature of the vapor feed stream in line 107 is preferably from 100° C. to 350° C., e.g., from 120° C. to 310° C. or from 150° C. to 300° C. Any feed that is not vaporized is removed from vaporizer 106 and may be recycled or discarded thereto. In addition, although line 107 is shown as being directed to the top of reactor 108, line 107 may be directed to the side, upper portion, or bottom of reactor 108.

Reactor 108 contains the catalyst that is used in the hydrogenation of the carboxylic acid, preferably acetic acid. In one embodiment, one or more guard beds (not shown) may be used upstream of the reactor, optionally upstream of the vaporizer 106, to protect the catalyst from poisons or undesirable impurities contained in the feed or return/recycle streams. Such guard beds may be employed in the vapor or liquid streams. Suitable guard bed materials may include, for example, carbon, silica, alumina, ceramic, or resins. In one aspect, the guard bed media is functionalized, e.g., silver functionalized, to trap particular species such as sulfur or halogens. During the hydrogenation process, a crude ethanol product stream is withdrawn, preferably continuously, from reactor 108 via line 109.

The crude ethanol product stream in line 109 may be condensed and fed to a separator 110, which, in turn, provides a vapor stream 111 and a liquid stream 112. In some embodiments, separator 110 may comprise a flasher or a knockout pot. The separator 110 may operate at a temperature of from 20° C. to 250° C., e.g., from 30° C. to 225° C. or from 60° C. to 200° C. The pressure of separator 110 may be from 50 kPa to 2000 kPa, e.g., from 75 kPa to 1500 kPa or from 100 kPa to 1000 kPa. Optionally, the crude ethanol product in line 109 may pass through one or more membranes to separate hydrogen and/or other non-condensable gases.

The vapor stream 111 exiting separator 110 may comprise hydrogen and hydrocarbons, and may be purged and/or returned to reaction zone 101. When returned to reaction zone 101, vapor stream 111 is combined with the hydrogen feed 104 and co-fed to vaporizer 106. In some embodiments, the returned vapor stream 111 may be compressed before being combined with hydrogen feed 104.

The liquid stream 112 from separator 110 is withdrawn and pumped to the side of first column 120, also referred to as an "acid separation column." In one embodiment, the contents of liquid stream 112 are substantially similar to the crude ethanol product obtained from the reactor, except that the composition has been depleted of hydrogen, carbon dioxide, methane and/or ethane, which are removed by separator 110. Accordingly, liquid stream 112 may also be referred to as a crude ethanol product. Exemplary components of liquid stream 112 are provided in Table 2. It should be understood that liquid stream 112 may contain other components, not listed in Table 2.

TABLE 2

COLUMN FEED COMPOSITION
(Liquid Stream 112)

| | Conc. (wt. %) | Conc. (wt. %) | Conc. (wt. %) |
|---|---|---|---|
| Ethanol | 5 to 70 | 10 to 60 | 15 to 50 |
| Acetic Acid | <90 | 5 to 80 | 15 to 70 |

TABLE 2-continued

COLUMN FEED COMPOSITION
(Liquid Stream 112)

|  | Conc. (wt. %) | Conc. (wt. %) | Conc. (wt. %) |
|---|---|---|---|
| Water | 5 to 40 | 5 to 30 | 10 to 30 |
| Ethyl Acetate | <30 | 0.001 to 20 | 1 to 12 |
| Acetaldehyde | <10 | 0.001 to 3 | 0.1 to 3 |
| Acetal | <5 | 0.001 to 2 | 0.005 to 1 |
| Acetone | <5 | 0.0005 to 0.05 | 0.001 to 0.03 |
| Other Esters | <5 | <0.005 | <0.001 |
| Other Ethers | <5 | <0.005 | <0.001 |
| Other Alcohols | <5 | <0.005 | <0.001 |

The amounts indicated as less than (<) in the tables throughout present specification are preferably not present and if present may be present in trace amounts or in amounts greater than 0.0001 wt. %.

The "other esters" in Table 2 may include, but are not limited to, ethyl propionate, methyl acetate, isopropyl acetate, n-propyl acetate, n-butyl acetate or mixtures thereof. The "other ethers" in Table 2 may include, but are not limited to, diethyl ether, methyl ethyl ether, isobutyl ethyl ether or mixtures thereof. The "other alcohols" in Table 2 may include, but are not limited to, methanol, isopropanol, n-propanol, n-butanol or mixtures thereof. In one embodiment, the liquid stream 112 may comprise propanol, e.g., isopropanol and/or n-propanol, in an amount from 0.001 to 0.1 wt. %, from 0.001 to 0.05 wt. % or from 0.001 to 0.03 wt. %. In should be understood that these other components may be carried through in any of the distillate or residue streams described herein and will not be further described herein, unless indicated otherwise.

Optionally, crude ethanol product in line 109 or in liquid stream 112 may be further fed to an esterification reactor, hydrogenolysis reactor, or combination thereof. An esterification reactor may be used to consume residual acetic acid present in the crude ethanol product to further reduce the amount of acetic acid that would otherwise need to be removed. Hydrogenolysis may be used to convert ethyl acetate in the crude ethanol product to ethanol.

In FIGS. 1 and 2, line 112 is introduced in the lower part of first column 120, e.g., lower half or lower third. In first column 120, acetic acid, a substantial portion of the water, and other heavy components, if present, are removed from the composition in line 121 and are withdrawn, preferably continuously, as residue. The substantial portion of the water removed in the residue may vary depending on the composition of the crude ethanol product, which is a result of the acetic acid conversion and selectivity to ethanol. In one embodiment, 30 to 90% of the water in the crude ethanol product is removed in the residue, e.g., from 40 to 88% of the water or from 50 to 84% of the water. Some or all of the residue may be returned and/or recycled back to reaction zone 101. Recycling the acetic acid in line 121 to the vaporizer 106 may reduce the amount of heavies that need to be purged from vaporizer 106. Reducing the amount of heavies to be purged may improve efficiencies of the process while reducing byproducts.

First column 120 also forms a first distillate stream, which is withdrawn in line 122, and which may be condensed and refluxed, for example, at a ratio of from 5:1 to 50:1, e.g., from 10:1 to 40:1 or from 20:1: to 30:1. The first distillate stream may comprise acetaldehyde as well as ethanol, and ethyl acetate. Preferably, first distillate stream in line 122 is returned to reaction zone 101 and preferably fed to the vaporizer 106 or reactor 108. At high acetic acid conversion, e.g., about 99% or greater, the acetaldehyde concentration in the first distillate stream in line 122 may increase. Also, at high acetic acid conversion, the ethanol concentration in first distillate stream in line 122 may be greater than the ethyl acetate concentration. In addition, diethyl acetal concentrations may be higher in the first distillate stream in line 122 at acetic acid conversion of about 99%. When the acetic acid conversion is less than 90%, the ethyl acetate concentration in first distillate stream in line 122 may be greater than the ethanol concentration.

A sidestream 123 is also withdrawn from column 120. Sidestream 123 primary comprises ethanol. Preferably, sidestream 123 is withdrawn above the feed location of liquid stream 112 and below the top of column 120. The acetaldehyde and/or ethanol concentrations in the first distillate in line 122 may vary depending on where the sidestream 123 is withdrawn from column 120.

When column 120 is operated under about 170 kPa, the temperature of the residue exiting in line 121 preferably is from 90° C. to 130° C., e.g., from 95° C. to 120° C. or from 100° C. to 115° C. The temperature of the distillate exiting in line 122 preferably is from 60° C. to 90° C., e.g., from 65° C. to 85° C. or from 70° C. to 80° C. The temperature of the sidestream 116 preferably is from 82° C. to 100° C. at 100 kPa, e.g., from 82° C. to 86° C. at 100 kPa. In some embodiments, the pressure of first column 120 may range from 0.1 kPa to 510 kPa, e.g., from 1 kPa to 475 kPa or from 1 kPa to 375 kPa. Exemplary components of the distillate and residue compositions for first column 120 are provided in Table 3 below. It should also be understood that the overhead stream and residue may also contain other components, not listed, such as components in the feed. For convenience, the residue of the first column may also be referred to as the "first residue." The distillates or residues of the other columns may be referred to with similar numeric modifiers (second, third, etc.) in order to distinguish them from one another, but such modifiers should not be construed as requiring any particular separation order.

TABLE 3

FIRST COLUMN 120

|  | Conc. (wt. %) | Conc. (wt. %) | Conc. (wt. %) |
|---|---|---|---|
| Distillate |  |  |  |
| Acetaldehyde | 0.5 to 50 | 1 to 35 | 1 to 25 |
| Ethyl Acetate | 10 to 90 | 15 to 80 | 40 to 75 |
| Ethanol | 5 to 70 | 10 to 55 | 10 to 50 |
| Water | 0.5 to 20 | 1 to 15 | 1 to 12 |
| Diethyl Acetal | <5 | <2 | <0.01 |
| Sidestream |  |  |  |
| Ethanol | 40 to 90 | 45 to 85 | 50 to 80 |
| Water | 4 to 30 | 5 to 25 | 10 to 20 |
| Ethyl Acetate | 0.1 to 60 | 1 to 50 | 1 to 40 |
| Acetic Acid | <2 | <0.1 | <0.05 |
| Acetaldehyde | 0.001 to 5 | 0.01 to 3 | 0.1 to 2 |
| Diethyl Acetal | 0.001 to 5 | 0.01 to 3 | 0.1 to 2 |
| Residue |  |  |  |
| Acetic Acid | <60 | 0.1 to 40 | 2 to 30 |
| Water | 50 to 99 | 60 to 98 | 70 to 98 |
| Ethanol | <1 | <0.5 | <0.1 |

In FIG. 1, sidestream 123 comprising ethanol, ethyl acetal and water may be directly fed to second column 124, and preferably fed to the middle of the column. Second column 124, also referred to as the light ends column, separates the sidestream 123 into a second distillate 125, which comprises ethyl acetate, acetaldehyde, diethyl acetal, and a second residue 126, comprising ethanol, water and a very low diethyl acetal concentrations. The second residue 126 is fed into a third column 127, where it is separated into a third distillate 128 comprising ethanol, and a third residue 129 comprising water.

Optionally, a portion of the third residue in line 129 is recycled to second column 124 via optional line 130 and the remainder may be purged outside of the system. In some embodiments, second column 123 may be an extractive distillation column, and an extraction agent is added thereto via lines 130 and/or from an outside source in optional line 131. Extractive distillation is a method of separating close boiling components, such as azeotropes, by distilling the feed in the presence of an extraction agent. The extraction agent preferably has a boiling point that is higher than the compounds being separated in the feed. In preferred embodiments, the extraction agent is comprised primarily of water. As shown, in one optional embodiment the extraction agent comprises a portion of the third residue in line 130. Preferably, the recycled third residue in line 130 is fed to second column 124 at a point higher than the sidestream in line 123. In one embodiment, the recycled third residue in line 130 is fed near the top of second column 124 or fed, for example, above the feed in line 123 and below the reflux line from the condensed overheads. In a tray column, the third residue in line 130, comprising primarily water, is continuously added near the top of the second column 124 so that an appreciable amount of the third residue is present in the liquid phase on all of the trays below. In another embodiment, the extraction agent is fed from a source outside of the process 100 via optional line 131 to second column 124. Preferably this extraction agent comprises water.

The molar ratio of the water in the extraction agent to the ethanol in the feed to the second column 124 is preferably at least 0.5:1, e.g., at least 1:1 or at least 3:1. In terms of ranges, preferred molar ratios may range from 0.5:1 to 8:1, e.g., from 1:1 to 7:1 or from 2:1 to 6.5:1. Higher molar ratios may be used but with diminishing returns in terms of the additional ethyl acetate in the second distillate and decreased ethanol concentrations in the second column distillate.

In such optional embodiments, an additional extraction agent, such as water from an external source, dimethylsulfoxide, glycerine, diethylene glycol, 1-naphthol, hydroquinone, N,N'-dimethylformamide, 1,4-butanediol; ethylene glycol-1,5-pentanediol; propylene glycol-tetraethylene glycol-polyethylene glycol; glycerine-propylene glycol-tetraethylene glycol-1,4-butanediol, ethyl ether, methyl formate, cyclohexane, N,N'-dimethyl-1,3-propanediamine, N,N'-dimethylethylenediamine, diethylene triamine, hexamethylene diamine and 1,3-diaminopentane, an alkylated thiopene, dodecane, tridecane, tetradecane and chlorinated paraffins, may be added to second column 124. Some suitable extraction agents include those described in U.S. Pat. Nos. 4,379,028, 4,569,726, 5,993,610 and 6,375,807, the entire contents and disclosure of which are hereby incorporated by reference. The additional extraction agent may be combined with the recycled third residue in line 130 and co-fed to the second column 124. The additional extraction agent may also be added separately to the second column 124 via line 131.

Second column 124 may be a tray or packed column. In one embodiment, second column 124 is a tray column having from 5 to 70 trays, e.g., from 15 to 50 trays or from 20 to 45 trays. Although the temperature and pressure of second column 124 may vary, when at atmospheric pressure the temperature of the second residue exiting in line 126 preferably is from 60° C. to 90° C., e.g., from 70° C. to 90° C. or from 80° C. to 90° C. The temperature of the second distillate exiting in line 125 preferably is from 50° C. to 90° C., e.g., from 60° C. to 80° C. or from 60° C. to 70° C. Column 124 may operate at atmospheric pressure. In other embodiments, the pressure of second column 124 may range from 0.1 kPa to 510 kPa, e.g., from 1 kPa to 475 kPa or from 1 kPa to 375 kPa. Exemplary components for the distillate and residue compositions for second column 124 are provided in Table 4 below. It should be understood that the distillate and residue may also contain other components, not listed, such as components in the feed.

TABLE 4

| SECOND COLUMN 123 (FIG. 1) | | | |
|---|---|---|---|
| | Conc. (wt. %) | Conc. (wt. %) | Conc. (wt. %) |
| Distillate | | | |
| Ethyl Acetate | 10 to 99 | 25 to 95 | 50 to 93 |
| Acetaldehyde | <25 | 0.5 to 15 | 1 to 8 |
| Water | <25 | 0.5 to 20 | 4 to 16 |
| Ethanol | <30 | 0.001 to 15 | 0.01 to 5 |
| Diethyl acetal | <5 | 0.001 to 2 | 0.01 to 1 |
| Residue | | | |
| Water | 30 to 90 | 40 to 85 | 50 to 85 |
| Ethanol | 10 to 75 | 15 to 60 | 20 to 50 |
| Ethyl Acetate | <1 | <0.5 | <0.01 |
| Diethyl acetal | <1 | <0.5 | <0.01 |
| Acetaldehyde | <1 | <0.5 | <0.01 |

In one embodiment, the weight ratio of ethanol in the second residue to second distillate preferably is at least 3:1, e.g., at least 6:1, at least 8:1, at least 10:1 or at least 15:1. The byproducts shown in second residue, ethyl acetate, diethyl acetal and acetaldehyde may be in very low concentrations, e.g., from 10 to 600 wppm, or from 20 to 300 wppm. In one preferred embodiment, the total concentration of these byproducts is less than 200 wppm or less than 100 wppm. The present invention may achieve these low levels of byproducts in the second residue by removing acetaldehyde in the first column 120, as shown in FIG. 1.

In optional embodiments, the recycling of the third residue promotes the separation of ethyl acetate from the residue of the second column 124. For example, the weight ratio of ethyl acetate in the second residue to second distillate preferably is less than 0.4:1, e.g., less than 0.2:1 or less than 0.1:1. In optional embodiments that use an extractive distillation column with water as an extraction agent as the second column 123, the weight ratio of ethyl acetate in the second residue to ethyl acetate in the second distillate approaches zero. In one embodiment, all of the third residue may be recycled until process 100 reaches a steady state and then a portion of the third residue is recycled with the remaining portion being purged from the system 100. The composition of the second residue will tend to have lower amounts of ethanol than when the third residue is not recycled. As the third residue is recycled, the composition of the second residue, as provided in Table 4, comprises less than 30 wt. % of ethanol, e.g., less than 20 wt. % or less than 15 wt. %. The majority of the second residue preferably comprises water. Notwithstanding this effect, the optional extractive distillation step may also reduce the amount of ethyl acetate that is sent to the third column, which is highly beneficial in ultimately forming a highly pure ethanol product.

In FIG. 1, because water is fed to the second column 124, in the sidestream 123 or through an optional extractive agent, an additional column may be used to further separate ethanol and water. The third column 127, also referred to as the "product column," receives the second residue in line 126 in the lower part of third column 128, e.g., lower half or lower third. Third column 127 recovers ethanol, which preferably is substantially pure with respect to organic impurities and other than the azeotropic water content, as the distillate in line 128.

The distillate of third column 127 preferably is refluxed as shown in FIG. 1, for example, at a reflux ratio of from 1:10 to 10:1, e.g., from 1:3 to 3:1 or from 1:2 to 2:1. The third residue in line 129, which comprises primarily water, may be optionally returned to the second column 124 as an extraction agent as described above via optional line 130.

In further optional embodiments, when third residue being directly recycled to second column 124, third residue may also be returned indirectly, for example, by storing a portion or all of the third residue in a tank (not shown) or treating the third residue to further separate any minor components such as aldehydes, higher molecular weight alcohols, or esters in one or more additional columns (not shown). The third residue in line 130 is withdrawn from third column 127 at a temperature higher than the operating temperature of the second column 124. Preferably, the third residue in line 130 is integrated to heat one or more other streams prior to be returned to the second column 124. In one embodiment, recycling the third residue further reduces the aldehyde components in the second residue and concentrates these aldehyde components in second distillate in line 125 from which they can be purged or recycled to the reaction zone.

Third column 127 is preferably a tray column as described above and operates at atmospheric pressure or optionally at pressures above or below atmospheric pressure. The temperature of the third distillate exiting in line 128 preferably is from 60° C. to 110° C., e.g., from 70° C. to 100° C. or from 75° C. to 95° C. The temperature of the third residue in line 129 preferably is from 70° C. to 115° C., e.g., from 80° C. to 110° C. or from 85° C. to 105° C. Exemplary components of the distillate and residue compositions for third column 127 are provided in Table 5 below. It should be understood that the distillate and residue may also contain other components, not listed, such as components in the feed.

TABLE 5

THIRD COLUMN 127 (FIG. 1)

|  | Conc. (wt. %) | Conc. (wt. %) | Conc. (wt. %) |
|---|---|---|---|
| Distillate |  |  |  |
| Ethanol | 75 to 96 | 80 to 96 | 85 to 96 |
| Water | <12 | 1 to 9 | 3 to 8 |
| Acetic Acid | <1 | <0.5 | <0.01 |
| Ethyl Acetate | <1 | <0.5 | <0.01 |
| Acetaldehyde | <1 | <0.5 | <0.01 |
| Diethyl Acetal | <1 | <0.5 | <0.01 |
| Residue |  |  |  |
| Water | 75 to 100 | 80 to 100 | 90 to 100 |
| Ethanol | <0.8 | 0.001 to 0.5 | 0.005 to 0.05 |
| Ethyl Acetate | <1 | 0.001 to 0.5 | 0.005 to 0.2 |
| Acetic Acid | <2 | 0.001 to 0.5 | 0.005 to 0.2 |

Any of the compounds that are carried through the distillation process from the feed or crude reaction product generally remain in the third distillate in amounts of less 0.1 wt. %, based on the total weight of the third distillate composition, e.g., less than 0.05 wt. % or less than 0.02 wt. %. In one embodiment, one or more sidestreams on third column 127 may remove impurities. The impurities may be purged and/or retained within the system 100.

The third distillate in line 128 may be further purified to form an anhydrous ethanol product stream, i.e., "finished anhydrous ethanol," using one or more additional separation systems, such as, for example, distillation columns, adsorption units, membranes, or molecular sieves. Suitable adsorption units include pressure swing adsorption units and thermal swing adsorption unit.

Returning to second column 124, the second distillate in line 125 preferably is refluxed as shown in FIG. 1, optionally at a reflux ratio of 1:10 to 10:1, e.g., from 1:5 to 5:1 or from 1:3 to 3:1. The second distillate in line 125 may be purged from the reaction zone 101. In some embodiments, it may be advantageous to return a portion of second distillate to reaction zone 101. In one embodiment, a portion of second distillate may be further separated to produce an acetaldehyde-containing stream and an ethyl acetate-containing stream. This may allow a portion of either the acetaldehyde-containing stream or ethyl acetate-containing stream to be recycled to reactor 103, while purging the other stream. The purge stream may be valuable as a source of either ethyl acetate and/or acetaldehyde. In addition, prior to returning to the reaction zone 101, the ethyl acetate and/or acetaldehyde in the second distillate may be further reacted in hydrogenation reactor 103 or in a secondary reactor. The outflow from the secondary reactor may be fed to reactor 103 to produce additional ethanol or to any of the distillation columns to recover additional ethanol.

FIG. 2 illustrates another exemplary separation system which produces an ethanol intermediate stream with a reduced concentration of aldehyde and/or diethyl acetal. The reaction zone 101 of FIG. 2 is similar to FIG. 1 and produces a liquid stream 112, e.g., crude ethanol product, that is fed to first column 120, as described above. Sidestream 123 from first column 120 is directed to a water separation unit 140 and the dehydrated sidestream 141 is fed to a second column 142 to remove light organics.

Water separation unit 140 may be an adsorption unit, membrane, molecular sieves, extractive column distillation, or a combination thereof. A membrane or an array of membranes may also be employed to separate water from the distillate. The membrane or array of membranes may be selected from any suitable membrane that is capable of removing a permeate water stream from a stream that also comprises ethanol and ethyl acetate.

In a preferred embodiment, water separator 140 is a pressure swing adsorption (PSA) unit. The PSA unit is optionally operated at a temperature from 30° C. to 160° C., e.g., from 80° C. to 140° C., and a pressure of from 0.01 kPa to 550 kPa, e.g., from 1 kPa to 150 kPa. The PSA unit may comprise two to five beds. Water separator 140 may remove at least 95% of the water from the portion of sidestream 123, and more preferably from 99% to 99.99% of the water. All or a portion of water stream 143 may be returned to column 120 in line 144, where the water preferably is ultimately recovered from column 120 in the first residue in line 121. Additionally or alternatively, all or a portion of water stream 143 may be purged. The remaining portion of sidestream exits the water separator 140 as an dehydrated sidestream 141. Dehydrated sidestream 141 may have a low concentration of water of less than 10 wt. %, e.g., less than 6 wt. % or less than 2 wt. %. In terms of ranges the water concentration of dehydrated sidestream 141 may be from 0.01 to 10 wt. %, e.g., from 0.01 to 6 wt. % or from 0.1 to 2 wt. %.

In one embodiment, a portion of sidestream 123 may bypass water separator 140 and may be fed to second column 142. To efficiently separate ethyl acetate in second column 142, a small portion of water in the feed may be beneficial. In some embodiments, the combined feeds to the second column have a water concentration of greater than 0.5 wt. %, e.g., greater than 2 wt. % or greater than 5 wt. %. In terms of ranges, the total water concentration of the combined overhead stream and ethanol mixture may be from 0.5 to 15 wt. %, e.g., from 2 to 12 wt. %, or from 5 to 10 wt. %.

Second column 142 may operate in a similar manner as second column 124 of FIG. 1, except that lower concentrations of water are fed to second column 142 in FIG. 2. Second column 124 produces a second distillate in line 145 comprising ethyl acetate, acetaldehyde, and/or diethyl acetal. Ethanol may be recovered in the second residue in line 146. Second column 142 may be a tray column or packed column. In one embodiment, second column 142 is a tray column having from 5 to 70 trays, e.g., from 15 to 50 trays or from 20 to 45 trays. Second column 142 operates at a pressure ranging from 0.1 kPa to 510 kPa, e.g., from 10 kPa to 450 kPa or from 50 kPa to 350 kPa. Although the temperature of second column 142 may vary, when at about 20 kPa to 70 kPa, the temperature of the second residue exiting in line 146 preferably is from 30° C. to 75° C., e.g., from 35° C. to 70° C. or from 40° C. to 65° C. The temperature of the distillate exiting in line 145 preferably is from 20° C. to 55° C., e.g., from 25° C. to 50° C. or from 30° C. to 45° C.

The total concentration of water fed to second column 142 preferably is less than 10 wt. %, as discussed above. When dehydrated sidestream in line 141 comprises minor amounts of water, e.g., less than 1 wt. % or less than 0.5 wt. %, additional water may be fed to the second column 142 as an extractive agent in the upper portion of the column. A sufficient amount of water is preferably added via the extractive agent such that the total concentration of water fed to second column 142 is from 1 to 10 wt. % water, e.g., from 2 to 6 wt. %, based on the total weight of all components fed to second column 142. If the extractive agent comprises water, the water may be obtained from an external source or from an internal return/recycle line from one or more of the other columns or water separators.

Exemplary components for the distillate and second residue compositions for the second column 142 are provided in Table 6, below. It should be understood that the distillate and residue may also contain other components, not listed in Table 6.

TABLE 6

SECOND COLUMN 142 (FIG. 2)

|  | Conc. (wt. %) | Conc. (wt. %) | Conc. (wt. %) |
|---|---|---|---|
| Distillate |  |  |  |
| Ethyl Acetate | 5 to 90 | 10 to 80 | 15 to 75 |
| Acetaldehyde | <60 | 1 to 40 | 1 to 35 |
| Ethanol | <45 | 0.001 to 40 | 0.01 to 35 |
| Water | <20 | 0.01 to 10 | 0.1 to 5 |
| Diethyl acetal | <5 | 0.001 to 2 | 0.01 to 1 |
| Second Residue |  |  |  |
| Ethanol | 80 to 99.9 | 85 to 99.5 | 90 to 99 |
| Water | <20 | 0.001 to 15 | 0.01 to 10 |
| Acetic Acid | <1 | <0.5 | <0.01 |
| Ethyl Acetate | <1 | <0.5 | <0.01 |
| Acetaldehyde | <1 | <0.5 | <0.01 |
| Diethyl Acetal | <1 | <0.5 | <0.01 |

Similar to second distillate in line 125 of FIG. 1, the second distillate in line 145 of FIG. 2, may be returned, in part or whole, to the reaction zone 101. The second residue in line 146 of FIG. 2 is an ethanol product stream that may be used or further dehydrated to remove water as described above with third distillate 126 in FIG. 1.

In another embodiment of the present invention, the intermediate ethanol stream may be obtained by partially condensing the overhead of the first column. In such embodiments, acetaldehyde may be vented from the non-condensed portion of the overhead. FIG. 3 illustrates a system that comprises a reaction zone 101 as described above and a first column 120. In FIG. 3, first column 120 produces a first distillate 122 that comprises primarily ethanol, as well as ethyl acetate, acetaldehyde, water, or diethyl acetal. A condenser 150 partially condenses first distillate and the partially condensed first distillate is collected in an overhead receiver 151. The non-condensed portion of first distillate may be vented from overhead receiver 151 in line 152. The vent in line 152 may comprise acetaldehyde, as well as ethanol, ethyl acetate, or diethyl acetal. Preferably, the vent in line 152 is returned to reaction zone 101. The condensed portion of first distillate, is withdrawn from overhead receiver in line 153 and refluxed to first column 120 at a reflux ratio from 10:1 to 1:10, e.g., from 3:1 to 1:3 or from 1:2 to 2:1. The condensed portion of first distillate in line 153 may be further separated by directly feeding to a second column as shown in FIG. 1, or by removing water as shown in FIG. 2.

Some of the residues withdrawn from the separation zone 102 comprise acetic acid and water. Depending on the amount of water and acetic acid contained in the residue of first column 120 may be treated in one or more of the following processes. The following are exemplary processes for further treating the residue and it should be understood that any of the following may be used regardless of acetic acid concentration. When the residue comprises a majority of acetic acid, e.g., greater than 70 wt. %, the residue may be recycled to the reactor without any separation of the water. In one embodiment, the residue may be separated into an acetic acid stream and a water stream when the residue comprises a majority of acetic acid, e.g., greater than 50 wt. %. Acetic acid may also be recovered in some embodiments from the residue having a lower acetic acid concentration. The residue may be separated into the acetic acid and water streams by a distillation column or one or more membranes. If a membrane or an array of membranes is employed to separate the acetic acid from the water, the membrane or array of membranes may be selected from any suitable acid resistant membrane that is capable of removing a permeate water stream. The resulting acetic acid stream optionally is returned to the reactor 108. The resulting water stream may be used as an extractive agent or to hydrolyze an ester-containing stream in a hydrolysis unit.

In other embodiments, for example, where the residue comprises less than 50 wt. % acetic acid, possible options include one or more of: (i) returning a portion of the residue to reactor 108, (ii) neutralizing the acetic acid, (iii) reacting the acetic acid with an alcohol, or (iv) disposing of the residue in a waste water treatment facility. It also may be possible to separate a residue comprising less than 50 wt. % acetic acid using a weak acid recovery distillation column to which a solvent (optionally acting as an azeotroping agent) may be added. Exemplary solvents that may be suitable for this purpose include ethyl acetate, propyl acetate, isopropyl acetate, butyl acetate, vinyl acetate, diisopropyl ether, carbon disulfide, tetrahydrofuran, isopropanol, ethanol, and $C_3$-$C_{12}$ alkanes. When neutralizing the acetic acid, it is preferred that the residue comprises less than 10 wt. % acetic acid. Acetic acid may be neutralized with any suitable alkali or alkaline earth metal base, such as sodium hydroxide or potassium hydroxide. When reacting acetic acid with an alcohol, it is preferred that the residue comprises less than 50 wt. % acetic acid. The alcohol may be any suitable alcohol, such as methanol, ethanol, propanol, butanol, or mixtures thereof. The reaction forms an ester that may be integrated with other systems, such as carbonylation production or an ester production process. Preferably, the alcohol comprises ethanol and the resulting ester comprises ethyl acetate. Optionally, the resulting ester may be fed to the hydrogenation reactor.

In some embodiments, when the residue comprises very minor amounts of acetic acid, e.g., less than 5 wt. %, the residue may be disposed of to a waste water treatment facility without further processing. The organic content, e.g., acetic acid content, of the residue beneficially may be suitable to feed microorganisms used in a waste water treatment facility.

The columns shown in figures may comprise any distillation column capable of performing the desired separation and/or purification. Each column preferably comprises a tray column having from 1 to 150 trays, e.g., from 10 to 100 trays, from 20 to 95 trays or from 30 to 75 trays. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or they may be arranged in two or more columns such that the vapor from the first section enters the second section while the liquid from the second section enters the first section, etc.

The associated condensers and liquid separation vessels that may be employed with each of the distillation columns may be of any conventional design and are simplified in the figures. Heat may be supplied to the base of each column or to a circulating bottom stream through a heat exchanger or reboiler. Other types of reboilers, such as internal reboilers, may also be used. The heat that is provided to the reboilers may be derived from any heat generated during the process that is integrated with the reboilers or from an external source such as another heat generating chemical process or a boiler. Although one reactor and one flasher are shown in the figures, additional reactors, flashers, condensers, heating elements, and other components may be used in various embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in the columns may vary. As a practical matter, pressures from 10 kPa to 3000 kPa will generally be employed in these zones although in some embodiments subatmospheric pressures or superatmospheric pressures may be employed. Temperatures within the various zones will normally range between the boiling points of the composition removed as the distillate and the composition removed as the residue. As will be recognized by those skilled in the art, the temperature at a given location in an operating distillation column is dependent on the composition of the material at that location and the pressure of column. In addition, feed rates may vary depending on the size of the production process and, if described, may be generically referred to in terms of feed weight ratios.

The ethanol product obtained by the process of the present invention may be an industrial ethanol product, i.e., an ethanol product suitable for industrial uses, comprising less than 12 wt. % water, e.g. less than 9 wt. % or less than 8 wt. %. The ethanol product may also be a fuel grade ethanol, suitable as an industrial fuel or in a blended fuel, e.g., blended with gasoline. Fuel grade ethanol typically comprises less water than industrial grade ethanol and may comprises less than 3 wt. % water, e.g., less than 2 wt. % or less than 0.5 wt. %. Exemplary ethanol product compositional ranges are provided below in Table 7.

TABLE 7

ETHANOL PRODUCT

| Component | Conc. (wt. %) | Conc. (wt. %) | Conc. (wt. %) |
| --- | --- | --- | --- |
| Ethanol | 88 to 99.9 | 90 to 99.5 | 93 to 99.5 |
| Water | <12 | 0.1 to 9 | 0.4 to 7 |
| Acetic Acid | <0.1 | <0.01 | <0.005 |
| Ethyl Acetate | <0.1 | <0.05 | <0.01 |
| Acetal | <0.1 | <0.05 | <0.005 |
| Acetone | <0.05 | <0.01 | <0.005 |
| Isopropanol | <0.5 | <0.1 | <0.05 |
| n-propanol | <0.5 | <0.1 | <0.05 |

In addition to low concentration of ethyl acetate, acetic acid, acetaldehyde, and/or diethyl acetal, the ethanol product of the present invention preferably contains very low amounts, e.g., less than 0.5 wt. %, of other alcohols, such as methanol, butanol, isobutanol, isoamyl alcohol and other $C_4$-$C_{20}$ alcohols. In one embodiment, the amount of isopropanol in the ethanol product is from 80 to 1,000 wppm, e.g., from 95 to 1,000 wppm, from 100 to 700 wppm, or from 150 to 500 wppm. In one embodiment, the ethanol product is substantially free of acetaldehyde, optionally comprising less than 8 wppm acetaldehyde, e.g., less than 5 wppm or less than 1 wppm.

The ethanol product produced by the embodiments of the present invention may be used in a variety of applications including fuels, solvents, chemical feedstocks, pharmaceutical products, cleansers, sanitizers, hydrogenation transport or consumption. In fuel applications, the finished ethanol composition may be blended with gasoline for motor vehicles such as automobiles, boats and small piston engine aircraft. The ethanol may also be used as an industrial fuel. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamine, ethyl benzene, aldehydes, and higher alcohols, especially butanol. In the production of ethyl acetate, the finished ethanol composition may be esterified with acetic acid. In another application, the finished ethanol composition may be dehydrated to produce ethylene. Any known dehydration catalyst can be employed to dehydrate ethanol, such as those described in copending U.S. Pub. Nos. 2010/0030002 and 2010/0030001, the entire contents and disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Yin U.S. Pat. No. 3,130,007, the entireties of which are hereby incorporated herein by reference.

In order that the invention disclosed herein may be more efficiently understood, an example is provided below. It should be understood that these examples are for illustrative purposes only and is not to be construed as limiting the invention in any manner.

EXAMPLES

The following examples were prepared with ASPEN Plus 7.1 simulation software to test various feed composition and separation systems.

Example 1

An ethanol reaction mixture obtained from converting 90% of the acetic acid is fed to an acid column as a liquid stream. The acid column operated with 72 trays with a feed stage at tray 51. Run A, B, and C were conducted that have a side-stream with different reflux ratios. For each run, the side-stream was withdrawn above the feed stage. To demonstrate the improvement in acetaldehyde concentration with the side-stream, Run D was conducted without a side stream. The reflux ratio of Run D was much lower due to the lack of a sidestream. For comparison the flow rate of the sidestreams in Runs A, B, and C, is similar to the flow rates of the distillate in Run D. Table 8 summarizes the results of example 1.

TABLE 8

|  | Run A | Run B | Run C | Run D |
|---|---|---|---|---|
| Reflux Ratio | 20 | 30 | 40 | 0.5 |
| Distillate |  |  |  |  |
| Acetaldehyde | 4.1 wt. % | 5.9 wt. % | 7.6 wt. % | 0.43 wt. % |
| Ethanol | 17.2 wt. % | 16.7 wt. % | 16.3 wt. % | 50.3 wt. % |
| Ethyl Acetate | 72.7 wt. % | 71.5 wt. % | 70.3 wt. % | 40 wt. % |
| Water | 6 wt. % | 5.9 wt. % | 5.8 wt. % | 8.9 wt. % |
| Diethyl Acetal | 0.01 wt. % | <0.01 wt. % | <0.01 wt. % | 0.27 wt. % |
| Sidestream |  |  |  |  |
| Ethanol | 49.9 wt. % | 50 wt. % | 50.1 wt. % | N/A |
| Ethyl Acetate | 38.2 wt. % | 38.7 wt. % | 38.9 wt. % | N/A |
| Water | 11.3 wt. % | 10.7 wt. % | 10.4 wt. % | N/A |
| Acetaldehyde | 0.33 wt. % | 0.32 wt. % | 0.31 wt. % | N/A |
| Diethyl Acetal | 0.27 wt. % | 0.27 wt. % | 0.28 wt. % | N/A |
| Ethanol Recovery | 99.2% | 99.4% | 99.5% | 99.9% |
| Acid Leakage | 0 wppm | 0 wppm | 0 wppm | 0 wppm |
| Diethyl Acetal Reacted | 31.1% | 31.2% | 30.4% | 33.1% |

Runs A, B, and C, demonstrate reduced aldehyde concentrations in the sidestream as compared to the distillate in Run D. Thus, less acetaldehyde is feed to the next separation unit for recovering ethanol.

Example 2

An ethanol reaction mixture obtained from converting 99% of the acetic acid is fed to an acid column as a liquid stream. The acid column operated with 72 trays with a feed stage at tray 51. Run E and F were conducted that have a sidestream with different reflux ratios. Runs E and F withdrew the sidestream above the feed stage and Run G was below the feed stage. To demonstrate the improvement in acetaldehyde concentration with the sidestream, Run H was conducted without a side stream. The reflux ratio of Run H was much lower due to the lack of a sidestream. For comparison the flow rate of the sidestreams in Runs E, F, and G, is similar to the flow rates of the distillate in Run H. Table 9 summarizes the results of Example 2.

Runs E, F, and G, demonstrate reduced aldehyde concentrations in the sidestream as compared to the distillate in Run H. Thus, less acetaldehyde is feed to the next separation unit for recovering ethanol. Withdrawing the sidestream below the feed point in Run G resulted in less ethanol recovery and higher acid leakage into the sidestream, but the acetaldehyde concentration was reduced.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

TABLE 9

|  | Run E | Run F | Run G | Run H |
|---|---|---|---|---|
| Reflux Ratio | 20 | 30 | 20 | 0.5 |
| Distillate |  |  |  |  |
| Acetaldehyde | 27.9 wt. % | 34.9 wt. % | 92.5 wt. % | 2.39 wt. % |
| Ethanol | 44.2 wt. % | 31.3 wt. % | 0.3 wt. % | 80.9 wt. % |
| Ethyl Acetate | 24.2 wt. % | 30.7 wt. % | 6.5 wt. % | 2.9 wt. % |
| Water | 3.3 wt. % | 2.7 wt. % | 0.7 wt. % | 12.4 wt. % |
| Diethyl Acetal | 0.4 wt. % | 0.4 wt. % | <0.01 wt. % | 1.5 wt. % |
| Sidestream Withdrawal | Above | Above | Below | N/A |
| Sidestream |  |  |  |  |
| Ethanol | 79.6 wt. % | 79.8 wt. % | 74.3 wt. % | N/A |
| Ethyl Acetate | 2.3 wt. % | 2.1 wt. % | 2.7 wt. % | N/A |
| Water | 14.9 wt. % | 15 wt. % | 21.3 wt. % | N/A |
| Acetaldehyde | 1.8 wt. % | 1.6 wt. % | 0.35 wt. % | N/A |
| Diethyl Acetal | 1.4 wt. % | 1.5 wt. % | 1.26 wt. % | N/A |
| Ethanol Recovery | 98.8% | 99.1% | 92.1% | 99.9% |
| Acid Leakage | 0 wppm | 0 wppm | 647 wppm | 0 wppm |
| Diethyl Acetal Reacted | 36% | 33.8% | 45.1% | 34% |

We claim:

1. A process for producing ethanol, the process comprising the steps of:
    hydrogenating a feed stream comprising an alkanoic acid and/or an ester thereof in the presence of a catalyst in a reactor to form a crude ethanol product comprising ethanol, ethyl acetate, water, and acetaldehyde;
    separating at least a portion of the crude ethanol product in a first distillation column into a first distillate comprising acetaldehyde, a sidestream comprising ethanol, and ethyl acetate, and a first residue stream comprising water; and
    recovering ethanol from the sidestream.

2. The process of claim 1, wherein the recovered ethanol comprises less than 1 wt. % diethyl acetal.

3. The process of claim 1, wherein the crude ethanol product comprises at least one acetal compound, and the process further comprises hydrolyzing the least one acetal compound in the first distillation column.

4. The process of claim 1, further comprising separating the sidestream in a second distillation column to yield a second distillate comprising ethyl acetate and a second residue comprising ethanol and water.

5. The process of claim 4, further comprising separating the second residue in a third column to yield a third distillate comprising ethanol and a third residue comprising water.

6. The process of claim 4, returning a portion of the third residue to the second distillation column.

7. The process of claim 1, further comprising removing water from the sidestream to produce a dehydrated sidestream.

8. The process of claim 7, further comprising separating the dehydrated sidestream in a second distillation column to yield a distillate comprising ethyl acetate and a second residue comprising ethanol.

9. The process of claim 8, wherein at least a portion of the second distillate is returned to the reactor.

10. The process of claim 1, wherein the crude ethanol product further comprises water, and the process further comprises separating a substantial portion of the water in the first residue.

11. The process of claim 1, wherein the sidestream comprises from 40 to 90 wt. % ethanol, from 0.1 to 60 wt. % ethyl acetate, from 0.001 to 5 wt. % acetaldehyde, and from 0.001 to 5 wt. % diethyl acetal.

12. The process of claim 1, wherein the crude ethanol product further comprises diethyl acetal, and the process further comprises decomposing at least 10 to 75% of the diethyl acetal fed to the first distillation column.

13. The process of claim 1, wherein at least a portion of the first distillate is returned to the reactor.

14. The process of claim 1, wherein the alkanoic acid is formed from methanol and carbon monoxide, wherein each of the methanol, the carbon monoxide, and hydrogen for the hydrogenating step is derived from syngas, and wherein the syngas is derived from a carbon source selected from the group consisting of natural gas, oil, petroleum, coal, biomass, and combinations thereof.

15. A process for producing ethanol, the process comprising the steps of:
    hydrogenating a feed stream comprising an alkanoic acid and/or an ester thereof in the presence of a catalyst in a reactor to form a crude ethanol product comprising ethanol, ethyl acetate, alkanoic acid, and acetaldehyde;
    separating at least a portion of the crude ethanol product in a first distillation column into a first distillate comprising acetaldehyde, a sidestream comprising ethanol, and ethyl acetate, and a first residue stream comprising alkanoic acid; and
    recovering ethanol from the sidestream.

16. A process for producing ethanol, the process comprising the steps of:
    providing a crude ethanol product comprising ethanol, ethyl acetate, alkanoic acid, water, and acetaldehyde;
    separating at least a portion of the crude ethanol product in a first distillation column into a first distillate comprising acetaldehyde, a sidestream comprising ethanol and ethyl acetate, and a first residue stream comprising alkanoic acid and water; and
    recovering ethanol from the sidestream.

* * * * *